(12) United States Patent
Shah et al.

(10) Patent No.: US 6,203,974 B1
(45) Date of Patent: *Mar. 20, 2001

(54) CHEMILUMINESCENT IMMUNOASSAY FOR DETECTION OF ANTIBODIES TO VARIOUS VIRUSES

(75) Inventors: Dinesh O. Shah, Libertyville; James P. Mackowiak, Grayslake; Natalie Dubovoy, Morton Grove, all of IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,093

(22) Filed: Sep. 3, 1998

(51) Int. Cl.⁷ .................................................. C12Q 1/70
(52) U.S. Cl. .................. 435/5; 435/7.1; 435/7.5; 435/7.9; 435/7.91; 435/7.94; 435/968; 435/969; 435/971; 435/974; 435/975; 436/501; 436/518; 436/546; 436/172
(58) Field of Search .................. 435/5, 7.1, 7.5, 435/7.9, 7.91, 7.94, 968, 969, 971, 974, 975; 436/501, 518, 546, 172

(56) References Cited

U.S. PATENT DOCUMENTS

| | | |
|---|---|---|
| 4,228,237 | 10/1980 | Hevey et al. . |
| 4,230,683 * | 10/1980 | Decker et al. .................. 424/1 |
| 4,495,296 * | 1/1985 | Neurath et al. .................. 436/530 |
| 4,927,769 | 5/1990 | Chang et al. . |
| 4,959,182 | 9/1990 | Schaap . |
| 5,006,309 | 4/1991 | Khalil et al. . |
| 5,015,157 | 5/1991 | Pinkerton et al. . |
| 5,066,782 * | 11/1991 | Montagnier et al. .................. 530/324 |
| 5,089,424 | 2/1992 | Khalil et al. . |
| 5,198,368 | 3/1993 | Khalil et al. . |
| 5,232,669 | 8/1993 | Pardinas . |
| 5,244,630 | 9/1993 | Khalil et al. . |
| 5,299,446 | 4/1994 | Pardinas et al. . |
| 5,550,027 | 8/1996 | Winkler et al. .................. 435/7.22 |
| 5,705,330 | 1/1998 | Shah et al. . |

FOREIGN PATENT DOCUMENTS

| | | |
|---|---|---|
| 0160900 | 4/1985 | (EP) . |
| 0254051 | 6/1987 | (EP) . |
| 0273115 | 10/1987 | (EP) . |
| 8906650 | 7/1989 | (WO) . |
| 9208979 | 5/1992 | (WO) . |
| 9501457 | 1/1995 | (WO) . |
| 9632004 | 10/1996 | (WO) . |

OTHER PUBLICATIONS

W.R. Seitz, "Immunoassay Labels Based on Chemiluminescence and Bioluminescence," *Clinical Biochemistry* 17:120–126 (1984).

Schuster and Schmidt in "Chemiluminescence of Organic Compounds," V. Gold and D. Bethel, eds., *Advances in Physical Organic Chemistry* 18:187–238, Academic Press, New York (1982).

Weeks et al., in :Acridinium Esters as Highly Specific Activity Labels in Immunoassays, *Clin. Chemistry* 19:1474–1478 (1984).

Bronstein et al., *J. Bioluminescence and Chemiluminescence* 4:99 (1988).

Clinical Chemistry 40 [11] :2112 (1994).

Ratner, L., et al., *Nature*, 313: 277–284. 1985.

Mandecki and Bolling, *Gene*, 68:101–107 (1988).

Kuhnel, et al., *Proc. Natl. Acad. Sci. USA*, 86:2383–2387 (1989).

Scharfstein et al. "Trypanosoma Cruzi: Description of a Highly Purified Surface Antigen defined by Human Antibodies" *Journal of Immunology*, vol. 131, No. 2(Aug. 1983), pp. 972–976. Abstract Only.*

Hartig et al. "Triple Immunofluorescence Labelling of Parvalbumin, Calbindin–D28 and Calretinin in Rat and Monkey Brain", *Journal of Neuroscience Methods*,vol. 67, No. 2(Aug. 1996), pp89–95. Abstract Only.*

Ponder et al. "Immunohistochemical Demonstration of H2 Antigens in Mouses Tissue Sections" *Journal of Histochemistry and Cytochemistry*, vol. 31, No. 7(Jul. 1983), pp 911–919. Abstract Only. QP501. H523.*

* cited by examiner

Primary Examiner—Jeffrey Stucker
(74) Attorney, Agent, or Firm—Cheryl L. Becker

(57) ABSTRACT

The subject invention relates generally to immunoassays for detection of antibodies by use chemiluminescent compounds. More particularly, the subject invention relates to chemiluminescent immunoassays to detect antibodies wherein a precomplex mixture is created and a two-step assay is performed resulting in a greater signal.

30 Claims, No Drawings

CHEMILUMINESCENT IMMUNOASSAY FOR DETECTION OF ANTIBODIES TO VARIOUS VIRUSES

BACKGROUND OF THE INVENTION

1. Technical Field

The subject invention relates generally to immunoassays for detection of antibodies by use of chemiluminescent compounds. More particularly, the subject invention relates to chemiluminescent immunoassays to detect antibodies wherein a precomplex mixture is created and a two-step assay is performed resulting in a greater or comparable signal as compared to a three-step assay.

2. Background Information

Immunoassays that employ chemiluminescent labels as the signal generating compound are known. For example, the application of chemiluminescence generation and detection for immunoassays has been reviewed by W. R. Seitz, "Immunoassay Labels Based on Chemiluminescence and Bioluminescence," *Clinical Biochemistry* 17:120–126 (1984).

A method for performing a chemiluminescent assay involving directly exciting and measuring a chemiluminescent signal emanating off an immune complex immobilized on or in a solid, porous element that is used as a separation means in a heterologous immunoassay and an apparatus for performing this measurement are described in U.S. Pat. No. 5,089,424 and now abandoned U.S. patent application Ser. No. 07/206,645 which both enjoy common ownership and are incorporated herein by referenece.

Additionally, a method for determining the presence of an analyte, in particular, HCV antibody, in a test sample by specific amplification of a chemiluminescent signal generated from a heterogeneous immunoassay which utilizes a precomplex is described in U.S. Pat. No. 5,705,330 which is herein incorporated in its entirety by reference.

The generation of light as a result of a chemical reaction is known in the art and was reviewed by Schuster and Schmidt in "Chemiluminescence of Organic Compounds," V. Gold and D. Bethel, eds., *Advances in Physical Organic Chemistry* 18:187–238, Academic Press, New York (1982). The use of acridinium compounds as labels for immunoassays and subsequent generation of short-lived chemiluminescence signals from these labels has been described in Weeks et al., in "Acridinium Esters as Highly Specific Activity Labels in Immunoassays," *Clin. Chemistry* 19:1474–1478 (1984). The use of stable acridinium sulfonamide esters has been described in a co-owned patent by Mattingly et al., U.S. Pat. No. 5,224,833 incorporated herein by reference and published as European Patent Appln. No. 0273115. The generation of long-lived luminescent signals has been described in the art as resulting from action of enzymes or nucleophilic agents on dioxetane compounds containing an adamantane structure. See, for example, European Patent Appln. No. 0254051; published PCT Patent Appln. No. WO 8906650; Bronstein et al., *J. Bioluminescence and Chemiluminescence* 4:99 (1988) and 5$^{th}$ International Conference on Biolumin. and Chemilumin., Florence-Bologna, Italy, Sep., 25–29 (1988). The use of a signal enhancer such as the use of avidin-biotin is also known. For example, U.S. Pat. No. 4,228,237 describes the use of a biotin-labeled specific binding substance for a ligand used in a method which also employs an enzyme labeled with avidin. The use of a biotin-avidin-biotin system is described in U.S. patent appln. Ser. No. 608,849 filed on May 10, 1984, now abandoned, which enjoys common ownership and is incorporated herein by reference (published on Nov. 13, 1985 as European Patent Appln. Ser. No. 160900). Methods of enhancing and amplifying the chemiluminescent signal generated in an immunoassay are known in the art. For example, U.S. Pat. No. 4,927,769 describes a method of enhancing the chemiluminescent signal generated from acridinium-ester labeled conjugates by the addition of surfactants. Also, U.S. Pat. No. 4,959,182 describes a method for amplifying the chemiluminescent signal generated from alkaline phosphatase-catalyzed 1,2-dioxetanes by the addition of a surfactant and a fluorescent compound attached to it.

Known traditional methods for performing chemiluminescence assays for detection of antibodies, if utilizing enhanced compounds as herein described, usually involve separated incubation steps for reacting the sample and capture reagent, reacting the sample/capture mixture with the conjugate to which it is attached and enhancer compound, and reacting the sample/capture/conjugate mixture with an enhancer-specific binding member, and then generating a signal.

In the present invention, it has been discovered that, by forming a precomplex of conjugate and probe (which terms are defined herein below) and performing a two-step assay for detection of antibodies to *Trypanosoma cruzi*, HTLV-1, HTLV-2, HIV-1 and HIV-2, a greater or comparable readout signal is generated, as compared to a three-step assay. With respect to a greater signal, such a signal enhances assay performance which improves assay sensitivity.

More specifically, *T. cruzi* is the causative agent of Chagas' disease, a major public health problem in Latin America and growing concern in the United States, as the number of infected immigrants increases. There is currently no testing of U.S. blood products for *T. cruzi* infection. The best tests available, although highly sensitive, are not of high enough specificity to be useful for widespread screening of the blood supply in this country. Thus, the present invention provides a much needed immunoassay for detection of *T. cruzi* antibodies.

Human Immunodeficiency Virus Type I and Type II (HIV-1 and HIV-2, respectively) are the cause of a debilitating and lethal disease referred to as Autoimmune Deficiency Syndrome (AIDS). Since the viruses may be carried in blood or plasma, assays are required which are able to detect infected, donated blood or plasma in order to prevent recipients from contracting the disease. Further, assays are also required for the detection of HIV-1 and HIV-2 in infected individuals. The present assay allows for the detection of antibodies to these two deadly viruses.

Human T-Lymphotropic Virus Type I and Type II (HTLV-1 and HTLV-2, respectively) are retroviruses that appear to play a role in human cancers. These viruses may also be carried in the blood or plasma; thus, it is important that blood and plasma donations be screened in order to prevent transmission to susceptible donors. It is also important that those individuals infected with these viruses be diagnosed properly. The present assay allows for the detection of antibodies to HTLV-1 and HTLV-2.

All U.S. patents and publications referred to herein are hereby incorporated in their entirety by reference.

SUMMARY OF THE INVENTION

The present invention encompasses a method for determining the presence of a Chagas Disease analyte in a test sample by specific amplification of a chemiluminescent signal generated from a heterogeneous immunoasssay. This method comprises the steps of: a) contacting the analyte/analyte-specific binding member pair complexes with a precomplex wherein the precomplex comprises 1) a probe comprising an enhancer compound attached to an analyte-specific binding member and 2) a conjugate comprising a chemiluminescent signal generating compound attached to an enhancer-specific binding member; b)incubating the resulting mixture for a time and conditions sufficient to form analyte/analyte-specific binding member pair/precomplex complexes; c)separating the resulting analyte/analyte-specific binding member pair/precomplex complexes of step b from free, unbound precomplexes; and d) determining the presence of the Chagas Disease analyte in the test sample by measuring the detectable signal. The chemiluminescent signal generating compound may be an acridinium compound or a derivative thereof. The analyte may be an antibody or an antigen. The enhancer compound may be selected from the group consisting of a hapten, a fluorescent compound and di-nitrophenol. In particular, the enhancer compound may be biotin. The acridinium compound may be selected from the group consisting of an acridinium ester and an acridinium sulfonamide. Additionally, the analyte-specific binding member may be attached to a solid phase prior to step (a).

Additionally, the present invention includes a kit for detecting a Chagas Disease analyte, comprising a Chagas Disease antigen; and a single container containing a precomplex reagent wherein the precomplex reagent comprises 1) a probe which comprises an enhance compound and 2) a conjugate which comprises a chemiluminescent signal-generating compound, wherein the chemiluminescent signal-generating compound is an acridinium compound. Again, the enhancer compound may be selected from the group consisting of a hapten, a fluorescent compound and di-nitrophenol, and, in particular, it may be biotin. The acridinium compound may be selected from the group consisting of an acridinium ester and an acridinium sulfonamide.

Furthermore, the present invention encompasses a method for determining the presence of an HTLV analyte in a test sample by specific amplification of a chemiluminescent signal generated from a heterogeneous immunoasssay. This immunoassay comprises the steps of: a) incubating a test sample containing an HTLV analyte with an analyte-specific binding pair member for a time and under conditions sufficient to form analyte/analyte specific-binding member pair complexes; b) contacting the analyte/analyte-specific binding member pair complexes with a precomplex wherein said precomplex comprises 1) a probe comprising an enhancer compound attached to an analyte-specific binding member and 2) a conjugate comprising a chemiluminescent signal generating compound attached to an enhancer-specific binding member, and incubating said resulting mixture for a time and conditions sufficient to form analyte/analyte-specific binding member pair/precomplex complexes wherein the chemiluminescent signal generating compound is an acridinium compound or a derivative thereof; c) separating the resulting analyte/analyte-specific binding member pair/precomplex complexes of step b from free, unbound precomplexes; and d) determining the presence of the HTLV analyte in the test sample by measuring the detectable signal. The analyte may be an antibody or an antigen. The enhancer compound may be selected from the group consisting of a hapten, a fluorescent compound and di-nitrophenol. In particular, the enhancer compound may be biotin. The acridinium compound may be selected from the group consisting of an acridinium ester and an acridinium sulfonamide. The analyte-specific binding member may be attached to a solid phase prior to step (a).

Additionally, the present invention includes a kit for detecting a HTLV analyte, comprising a HTLV antigen; and a single container containing a precomplex reagent wherein the precomplex reagent comprises 1) a probe which comprises an enhance compound and 2) a conjugate which comprises a chemiluminescent signal-generating compound, wherein the chemiluminescent signal-generating compound is an acridinium compound. The enhancer compound may be selected from the group consisting of a hapten, a fluorescent compound and di-nitrophenol, and, in particular, it may be biotin. The acridinium compound may be selected from the group consisting of an acridinium ester and an acridinium sulfonamide.

The present invention also includes a method for determining the presence of an HIV analyte in a test sample by specific amplification of a chemiluminescent signal generated from a heterogeneous immunoasssay. This immunoassay comprises the steps of: a) incubating a test sample containing an HIV analyte with an analyte-specific binding pair member for a time and under conditions sufficient to form analyte/analyte specific-binding member pair complexes; b) contacting the analyte/analyte-specific binding member pair complexes with a precomplex wherein said precomplex comprises 1) a probe comprising an enhancer compound attached to an analyte-specific binding member and 2) a conjugate comprising a chemiluminescent signal generating compound attached to an enhancer-specific binding member, and incubating said resulting mixture for a time and conditions sufficient to form analyte/analyte-specific binding member pair/precomplex complexes, wherein the chemiluminescent signal generating compound is an acridinium compound or a derivative thereof; c) separating the resulting analyte/analyte-specific binding member pair/precomplex complexes of step b from free, unbound precomplexes; and d) determining the presence of said HIV analyte in said test sample by measuring the detectable signal. The analyte may be an antibody or an antigen. The enhancer compound may be selected from the group consisting of a hapten, a fluorescent compound and di-nitrophenol. The enhancer compound may be biotin. The acridinium compound may be selected from the group consisting of an acridinium ester and an acridinium sulfonamide. The analyte-specific binding member is attached to a solid phase prior to step (a).

The invention also includes a kit for detecting a HIV analyte, comprising a HIV antigen; and a single container containing a precomplex reagent wherein the precomplex reagent comprises 1) a probe which comprises an enhance compound and 2) a conjugate which comprises a chemiluminescent signal-generating compound, wherein said chemiluminescent signal-generating compound is an acridinium compound. The enhancer compound may be selected from the group consisting of a hapten, a fluorescent compound and di-nitrophenol. In particular, the enhancer compound may be biotin. The acridinium compound may be selected from the group consisting of an acridinium ester and an acridinium sulfonamide.

DETAILED DESCRIPTION OF THE INVENTION

The chemiluminescent properties of acridinium compounds and their use in immunoassays have been described. Immunochemical tracers with acridinium esters of acridinium sulfonamide labels can be triggered with and alkaline peroxide solution to produce a chemiluminescent signal that maximizes after approximately two seconds. Light emission is completely extinguished after approximately ten seconds. Acridinium sulfonamide labeling chemistry may be employed according to the invention for making a stable tracer of high quantum yield. This method is as described in pending U.S. patent application Ser. No. 371,763, now abandoned which enjoys common ownership and is incorporated herein by reference.

Alternatively, chemically catalyzed, long-lived 1,2-dioxetane chemiluminescence can be generated in a variety of ways. Thus, EP 0 254 051 (cited supra) describes a siloxy-substituted dioxetane as 4-(6 tert-butyldimethylsiloxy-2-naphthyl)-4-methoxyspiro[1,2-dioxetane-3,2'adamantane] that is triggered with tetrabutylammonium chloride solution to produce a chemiluminescent signal lasting for 20 minutes. Also, enzymes such as aryl esterase and alkaline phosphatase react with aryl dioxetane derivatives stabilized with an adamantane cage to produce similar long-lived chemiluminescent signals.

Also, WO 881 00694 (WO 8906650, cited supra) describes long-lived emissions from alkaline phosphatase catalyzed reactions of 3-(2'-spiroadamantane)-4-methoxy-4-(3'-phosphoryloxy)-phenyl-1,2-dioxetanes (AMPPD) and use of these compounds in an immunoassay. Thus, alkaline phosphatase labeling techniques are known and catalyzed dioxetane chemiluminescence may be used to generate long-lived signals.

The present invention provides three immunoassays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. A specific binding pair member also can include a combination of a conjugate (as defined herein below) and a probe (as defined herein below). Furthermore, specific binding pairs can include members that are analogs of the original specific binding members, for example, an analyte analog. Immunoreactive specific binding members include antigens, antigen fragments, antibodies and antibody fragments, both monoclonal and polyclonal, and complexes thereof, including those formed by recombinant DNA molecules.

The term "hapten", as used herein, refers to a partial antigen or non-protein binding member which is capable of binding to an antibody, but which is not capable of eliciting antibody formation unless coupled to a carrier protein.

"Analyte," as used herein is the substance to be detected which may be present in the test sample. The analyte can be any substance for which there exists a naturally occurring specific binding member (such as, an antibody) or for which a specific binding member can be prepared. Thus, an analyte is a substance that can bind to one or more specific binding members in an assay. "Analyte," also includes any antigenic substances, haptens, antibodies and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. The details for the preparation of such antibodies and the suitability for use as specific binding members are well known to those skilled in the art.

A "capture reagent," as used herein, refers to an unlabeled specific binding member which is specific either for the analyte as in a sandwich assay, or for an ancillary specific binding member, which itself is specific for the analyte as in an indirect assay. The capture reagent can be directly or indirectly bound to a solid phase material before the performance of the assay or during the performance of the assay, thereby enabling the separation of immobilized complexes from the test sample.

The "test sample" can be a sample of biological fluid such as whole blood components including red blood cells, white blood cells platelets, serum and plasma; ascites, urine, cerebrospinal fluid, and other constituents of the body which may contain the analyte of interest. Optionally, test samples may be obtained from water, soil and vegetation.

The term "probe," as used herein, means a member of the specific binding pair attached to an "enhancer compound". An "enhancer compound" can be any compound used in the assay which can enhance the signal generated by the chemiluminescent compound. Thus, enhancer compounds include haptens such as biotin, and also include fluorescein, dinitrophenol, and the like.

The "chemiluminescent" compound is meant to include all compound capable of generating a chemiluminescent signal such as acridinium esters, acridinium sulfonamides, phenanthridiniums, 1,2-dioxetanes, luminol, or enzymes that catalyze chemiluminescent substrates, and the like.

"Conjugate", as used herein means a chemiluminescent compound to which a compound specific for the enhancer compound (a specific binding member of the enhancer) is attached. For example, if the enhancer compound utilized is biotin, then anti-biotin, or avidin can be used as the enhancer-specific compound.

A solid phase may be used according to the method of the invention. A "solid phase," as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. As yet another alternative, the receptor molecule can be any specific binding member which is immobilized upon the solid phase and which has the ability to immobilize the capture reagent through a specific binding reaction. The receptor molecule enables the indirect binding of the capture reagent to a solid phase material before the performance of the assay or during the performance of the assay.

An assay device for the present invention can have many configurations, several of which are dependent upon the material chosen as the solid phase. For example, the solid phase can include any suitable porous material. By "porous" is meant that the material is one through which the test sample can easily pass and includes both bibulous and non-bibulous solid phase materials. In the present invention, the solid phase can include fiberglass, cellulose or nylon pad for use in a pour and flow-through assay device having one or more layers containing one or more of the assay reagents; a dipstick for a dip and read assay; a test strip for wicking (e. g., paper) or thin layer chromatographic or capillary action (e. g. polyethylene sheet material). The solid phase, however, is not limited to porous materials. The solid phase can also comprise polymeric or glass beads, microparticles, tubes, sheet, plates, slides, webs, tapes, test tubes, or the like or any other material which has an intrinsic charge or which can retain a charged substance.

Natural, synthetic, or naturally occurring materials that are synthetically modified, can be used as a solid phase including polysaccharides, e.g., cellulose materials such as paper and cellulose derivatives such as cellulose acetate and nitrocellulose; silica; inorganic materials such as deactivated alumina; diatomaceous earth, MgSO4, or other inorganic freely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton and synthetic (e.g., nylon); porous gels such as silica gel, agarose, dextran, and gelatin; polymeric films such as polyacrylamide; and the like. The solid phase should have reasonable strength or strength can be provided by means of a support, and it should nor interfere with the production of a detectable signal.

Preferred solid phase materials for flow-through assay devices include filter paper such as a porous fiberglass material or other fiber matrix materials. The thickness of such material is not critical, and will be a matter of choice, largely based upon the properties of the sample or analyte being assayed such as the fluidity of the test sample.

To change or enhance the intrinsic charge of the solid phase, a charged substance can be coated directly to the material or onto microparticles which are then retained by a solid phase support material. Alternatively, microparticles can serve as the solid phase, by being retained in a column or being suspended in the mixture of soluble reagents and test sample, or the particles themselves can be retained and immobilized by a solid phase support material. By "retained and immobilized" is meant that the particles on or in the support material are not capable of substantial movement to positions elsewhere within the support material. The particles can be selected by one skilled in the art from any suitable type of particulate material and include those composed of polystyrene, polymethylacrylate, polypropylene, latex, polytetrafluoroethylene, polyacrylonitrile, polycarbonate, or similar materials. The size of the particles is not critical, although it is preferred that the average diameter of the particles be smaller than the average pore size of the support material being used.

According to a preferred embodiment of this invention, a test sample which may contain the analyte to be detected is contacted with a binding pair member specific for the analyte the so-called "capture reagent," to form a mixture. This mixture is incubated for a time and under conditions sufficient for analyte/analyte specific binding pair member complexes to form. Then, these complexes are contacted with a precomplex of a pre-formed probe/conjugate mixture (the so-termed precomplex) comprising an enhancer compound attached to analyte specific binding pair member and a conjugate comprising a chemiluminescent signal generating compound conjugated to an enhancer compound binding member, to form a second mixture. This second mixture is incubated for a time and under conditions sufficient to form analyte/analyte/specific binding pair member/precomplex complexes. The presence of the analyte in the test sample is determined by measuring the signal generated by the chemiluminescent compound. Preferable, the capture reagent also may be attached to a solid phase. The preferred enhancer compound is biotin, while the preferred chemiluminescent compounds capable of generating a measurable signal are acridinium sulfonamides. The precomplex is a mixture of probe and conjugate which is reacted together (i.e., preformed complexes of probe/conjugate are made) before use in the assay. Test kits, comprising a container containing a precomplex reagent comprising a probe and conjugate. The kit also can include other reagents useful for performance of the assay, including containers of buffers for diluting sample, washing and mixing, and compounds which can trigger the chemiluminescent reaction, such as an alkaline peroxide activator solution when using acridinium compounds.

The present invention may be illustrated by the use of the following non-limiting examples:

EXAMPLE 1

PREPARATION OF ACRIDINIUM-LABELED ANTI-BIOTIN ANTIBODY

A. For Use in Three-Step Assay:

(i) Activation of Methyl Acridinium

An aliquot of an acridinium methyl ester (10-methyl-n-tosyl-n-(1-carboxymethyl)-9-acridinium carboxamide trifluoromethyl sulfonate (1.8 mg) (prepared as described in E.P.O. 0 273 115, published Jul. 6, 1988, incorporated herein by reference) was dissolved in 180 $\mu$l dimethylformamide (DMF. Pierce Chemical Co., Rockford, Ill.). The acridinium ester was activated by adding 88 $\mu$l of N-hydroxy succinimide (NHS. 5,75 mg/mL in DMF) and 88 $\mu$l of 1-ethyl-3-(3-dimethylaminopropyl) carbodiimide (EDAC. 9.75 mg/ml in DMF) to the dissolved acridinium. The molar ratio of EDAC to NHS was 1:1. The reaction was stirred at room temperature overnight in a light protected vial. Activation was confirmed by thin layer chromatography (TLC Silica Gel 60 F-254. Merck Darmstadt, Germany) using chloroform, DMF, and acetic acid as the developing solvent in 9:9:2 volume/volume ratio. The activated ester appeared as a new species with a greater Rf(~0.22) than the acridinium salt dissolved in DMF.

(ii) Conjugation of Anti-Biotin to Activated Methyl Acridinium

Thirty-six (36) $\mu$l of a conjugate buffer (CB, containing 0.1M sodium phosphate. 0.15M NaCl. 0.5% (3-[(3-cholamidopropyl)-dimethylammonio]-1-propane-sulfonate) (CHAPS®. Sigma Chemical Company, Saint Louis, Mo.), pH 8.0) and 8 $\mu$l of activated methyl acridinium ester solution (5 mg/mL) (prepared as described in Example I(A)(i)) was added to 200 $\mu$l of a 10 mg/ml concentration of a monoclonal anti-biotin antibody (*Clinical Chemistry* 40 [11]:2112 [1994]) at room temperature while stirring in an amber glass vial and mixed for 10 minutes. The reaction mixture then was centrifuged at 12,000 rpm for two minutes in a TD$_x$® microfuge (Abbott Laboratories, Abbott Park, Ill.) to remove aggregates. The supernatant next was applied to a 300×7.8 mm Bio-Sil™ SEC250 gel filtration column (Bio-Rad Richmond, Calif.) which had been equilibrated with buffer containing 0.1 mg/ml CHAPS. 120 mM NaCl and 10 mM sodium phosphate, pH 6.3. The column was eluted at 10 ml/min with the same buffer using a Beckman 421A controller equipped with a model 114M pump. Fractions of one ml were collected, and the absorbance determined at 280 nm and 370 nm with a Beckman DU-7 spectrophotometer. The extent of acridinium incorporation was calculated by measuring the protein concentration using the absorbance at 280 nm corrected for the contribution made by acridinium at this wavelength (corrected protein absorbance=$A_{280}-A_{370}X0.247$). Moles of acridinium and IgG were calculated using molar extinction coefficients of 14.650 and 220.000 $M^{-1}cm^{-1}$, respectively. The acridinium to IgG ratio (mole/mole) obtained was about 2. The conjugate was stored 40° C.

B. For Use in Two-Step Assay:

(i) Preparation of Pre-complexed Biotinylated Anti-Human F(ab')$_2$ and Acridinium-Labeled Anti-Biotin Conjugate Methyl Acridinium was labeled to anti-biotin as described hereinabove in Example I(A)(ii). Biotinylated F(ab')$_2$ fragment of anti-human IgG was purchased from Kirkergard and Perry (Gaithersburg, Md.). The degree of functional biotin incorporated to this biotinylated probe was determined by fluorescence polarization following the method described in *Clinical Chemistry* 40 (11):2112 (1994) and was found to be 8 moles biotin/mole of IgG.

Methyl acridinium labeled anti-biotin antibody was allowed to react with biotinylated F(ab')$_2$ probe to make a pre-complex by adding 90 µl of anti-biotin methyl acridinium (500 ug/ml) to 20 µl of biotinylated probe (500 mg/ml). This mixture was diluted with 390 µl of conjugate diluent (containing 0.04 g/ml bovine serum albumin (BSA), 0.01 g/mL Triton X-100®, 600 mM NaCl, 0.001 g/ml sodium azide in 10 mM phosphate, pH 6.3). Subsequently, this mixture was left at room temperature in the dark with occasional shaking for minutes. Then, 5 µl of the mixture was diluted with 7.995 ml of CB. Mixed and stored overnight at room temperature. This so-formed pre-complex was filtered through a 0.2 µm Nalgene® membrane. The filtered precomplex was stored at 2°–8° C. in the dark.

EXAMPLE II

PREPARATION OF COATED MICROPARTICLES FOR CHAGAS ASSAY

A solution of EDAC (100 µg/mL) and Chagas Organism Nitrogen Pressure-Lysed Antigen (100 µg/mL) (see insert corresponding to Abbott Chagas Antibody EIA Assay®, Abbott Laboratories, Abbott Park, Ill.; ATCC Control No. 30266) was mixed with 2-(N-morpholino) ethanesulfonic acid (MES) Buffer for 1 minute. The EDAC/Antigen mixture was then added to carboxylated polystyrene microparticles (1% weight/volume (0.191 micron from Saradyn, Indianapolis, Ind.), and incubated at room temperature for 6 to 16 hours. Coated microparticles were then washed with PBS/0.1% Tween20 Buffer by centrifugation, and a final dilution into Sucrose Buffer was made to a final concentration of 0.1% (w/v).

EXAMPLE III

CHAGAS THREE-STEP ASSAY

The three-step assay as well as all assays described herein were performed by using an instrument (Abbott Prism® instrument, Abbott Laboratories, Abbott Park, Ill.) as described herein. This instrument and related reagents, methods and disposable devices are described in detail in U.S. Pat. Nos. 5,089,424 and 5,120,199 as well as 5,006,309, 5,198,368, 5,232,669, 5,244,630, 5,246,354, 5,299,446, 5,015,157 and Des. 332,834, which are commonly owned and incorporated herein by reference.

At station 1 of the PRISM assay, 100 µL of control or sample, 50 µL of Specimen Diluent Buffer (SDB), and 50 µL of *Trypanosoma cruzi* lysate coated microparticles were dispensed into the incubation well of a reaction tray. At station 4, the reaction mixture was transferred to the glass fiber matrix of the reaction tray after 18 minutes of incubation at 37 degrees C. At station 5, 50 µL of biotinylated F(ab")2 fragment of anti-human IgG (probe, 12.5 ng/ml) were dispensed onto the glass fiber matrix of the reaction well. The tray was further incubated at 37 degrees for 10 minutes. At station 6, the transferred microparticles and excess probe were washed. At station 7, 50 ml of acridinium labeled anti-biotin conjugate (56.25 ng/ml) were dispersed onto the glass fiber matrix of the reaction tray. The tray was further incubated at 37 degrees Celsius for 10 minutes. At station 8, the excess conjugate was washed away (Wash 1 or Wash 2 in Table 1). At station 9, a chemiluminescence (CL) signal was activated by the addition of an alkaline hydrogen peroxide solution, and the photons were measured by a photomultiplier tube. The results are expressed as Positive to Negative (P/N) in Table I below.

EXAMPLE IV

CHAGAS TWO-STEP ASSAY

A two step assay was performed as set forth in Example III, with the following modifications:

At station 1, 50 µL of sample or control, 50 µL of Sample Diluent Buffer (SDB), and 50 µL of *Trypanosoma cruzi* lysated-coated microparticles (0.1%) were dispensed into the incubation well of a reaction tray. At station 4, the reaction mixture was transferred to the glass fiber matrix of the reaction tray after 18 minutes of incubation at 37 degrees C. At station 5, 50 µL of a pre-complex of biotinylated F(ab")2 fragment of anti-human IgG (probe) and acridinium-labeled anti-biotin was dispensed onto the fiber matrix of the reaction tray. The tray was further incubated for 23 minutes at 37 degrees C. At station 8, the excess complex was washed away (Wash 1 or Wash 2 in Table I). At station 9, as in all of the assays described below, a chemiluminescence (CL) signal was activated/generated (by addition of an alkaline hydrogen peroxide solution), and the photons were measured by a photomultiplier tube. The amount of light emitted is proportional to the amount of antibody in the sample. The presence or absence of antibody in the sample is determined by comparing the number of photons collected from the sample to a cutoff value determined from a calibration performed in the same batch. The results are expressed as Positive to Negative (P/N) in Table I below. The P/N is the average chemiluminescence count (n=2) of the test sample divided by the average chemiluminescence count of the negative sample (n=2).

TABLE I

CHAGAS 2-STEP ASSAY VERSUS 3-STEP ASSAY

| Wash 1 | | | | Wash 2 | | | |
|---|---|---|---|---|---|---|---|
| Two Step P/N* | Negs** | Three Step P/N | Negs | Two Step P/N | Negs | Three Step P/N | Negs |
| 16.05 | 2,219 | 1.21 | 40,423 | 8.81 | 1,479 | 1.07 | 38,124 |

*The P/N is the average chemiluminescence count (n = 2) of the test sample divided by the average chemiluminescence count (n = 2) of the negative sample (n = 2).
**Value for negative calibrator is represented in absolute counts.
Chagas Positive: Recalcified Human Plasma Positive for Chagas, Negative for Syphilis, HBSAg, HCV and HIV I and II.
Wash 1: MES/NaCl/Proclin: pH 5.7
Wash 2: Borate/LDS/Azide: pH 8.5

As the data demonstrate, the two step assay gave a significantly higher P/N than the three step assay, demonstrating the superiority of the two-step assay for Chagas testing.

EXAMPLE V

PREPARATION OF HIV-1 AND HIV-2 MICROPARTICLES

Microparticles coated with several recombinant antigens were prepared by coating three separate populations of microparticles with HIV antigens.

HIV Cell Banks:

1. pJC104XL (gp36)
2. pOM10/PV361 HIV-1 RP41 (gp41)
3. pKRR955/KRR136 E. coli (p24)

A. Preparation of Recombinant Proteins:

Recombinant E. coli clones containing the entire HIV-1 genome and HIV-2 env genes were derived from genomic proviral DNA. These fragments were used to subclone DNA fragments containing the HIV-1 env genes. These proteins were expressed in specific expression vectors in E. coli or B. megaterium. (See also insert corresponding to ABBOTT PRISM® HIV/HIV-2 assay, Abbott Laboratories, Abbott Park, Ill.)

I. Preparation of Initial HIV-1 and HIV-2 Clones:

a. HIV-1

An HIV-1 genomic library was prepared by ligating a partial EcoRI digestion of genomic DNA derived from HIV-1 infected HT-9 cells (obtained from Dr. Robert Gallo, National Cancer Institute, Laboratories of Tumor Cell Biology, Lot No. P3-21) with bacteriophage lambda Charon 4A EcoRI arms and transfecting into E. coli C600. The library was screened by hybridization with cDNA made from HIV-1 viral RNA, and a single phage (designated Phage 4B) was obtained containing the entire HIV-1 genome.

Phage 4B DNA was digested with KpnI and ligated into the KpnI site of pUC18 (Bethesda Research Laboratories, Bethesda, Md.). A clone (designated PcK2) containing the entire p41 region of the HIV-1 env was identified and mapped.

Phage 4B DNA was digested with EcoRI and ligated into the EcoRI site of pBR322. A clone (designated pcR23) containing the entire HIV-1 gag gene was identified and mapped.

b. HIV-2

A DNA fragment containing the env gene from HIV-2 prophage isolate D194.5 was identified within a lambda genomic library of prophage DNA. This fragment was subcloned into an EcoRI site of an E. coli expression vector (lambda $P_L$ vector pKH20). The resulting plasmid was named pEHa.

i. Construction of HIV-1 env Vector pOM10 (for Expression of Soluble HIV-1 gp41) and Introduction into a Host Cell:

The construction of the envelope expression vector was a two step process. The first step involved the construction of an E. coli plasmid containing a smaller DNA fragment containing env (designated gp41). The second step involved the construction of an expression vector with the ability to survive in both Escherichia sp. and Bacillus sp., and the introduction of the env fragment into this plasmid (designated a. Construction of plasmid p41C:

An 854 base pair (bp) BamHI/BgIII DNA fragment obtained from plasmid pcK2 was ligated into the BamHI site of pUC9 (Pharmacia). A clone containing a part of the env gene in the same orientation as the lacZ gene was identified, mapped and designated p41A. A 557 bp BamHI DNA fragment obtained from plasmid pcK2 was ligated into the BamHI site of plasmid p41A. A plasmid containing the complete rp41 sequence of the env gene in the same orientation as the lacZ gene was identified, mapped and designated p41C.

b. Construction of plasmid pAS14:

An E. coli plasmid containing the Bacillus sporulation promoter spoVG (developed by Dr. R. Losick, Harvard University and designated pVG1) was restricted with SmaI. This DNA fragment was ligated into the Bacillus plasmid pE194 which had previously been restricted with XbaI. Blunt ends were formed using E. coli DNA polymerase 1 (Klenow fragment) to fill in the "sticky" DNA ends (blunt-end treatment). A plasmid (designated pAS5) was isolated, mapped and shown to have the ability to survive in both E. coli and B. subtilis. The env gene was then inserted into pAS5. A DNA fragment from the plasmid p41C containing the env gene was generated via EcoRI/SalI digestion and subsequent blunt-end treatment. This DNA fragment was ligated to plasmid pAS5 which had been linearized with SalI and blunt-end treated. The clone designated pAS14 was determined to have the env gene fused to the spoVG promoter in the proper orientation.

c. Construction of plasmid pOM10:

Finally, the erythromycin resistance gene in pAS14 was replaced by the chloramphenicol resistance gene from a related Bacillus plasmid pC194 as follows. A 1107 bp DNA fragment containing the chloramphenicol acetyl transferase (CAT) gene from a ClaI/DraI digest of the plasmid pC194 was isolated. This DNA fragment was ligated to the 6407 bp DNA fragment isolated from a ClaI/SmaI digestion of pAS14 (a treatment which removes all of the original erythromycin resistance gene). The final plasmid obtained was designated pOM10.

d. Complete DNA sequence of plasmid pOM10:

The promoter region, transcriptional start and ribosomal binding site span based 4840–4971. The coding region (bases 4972–6183) consists of sequences derived from the spoVG region of the parent plasmid pVG1 (bases 4972–5004), sequences derived during DNA ligations (bases 5005–5010) and sequences derived from the HIV-1 gp120 (env) gene (bases 5001–5145) (Ratner, L., et al., *Nature*, 313:277–284, 1985). The rp41 sequences are from bases 5146–6180. The translation is terminated at the native termination codon of the env gene (bases 6181–6183). The DNA sequence coding for the recombinant protein was confirmed by sequencing of the plasmid isolated from production scale fermentation.

e. Recombinant protein encoded by plasmid pOM10

Plasmid pOM10 expresses the HIV-1 envelope protein as a fusion protein containing 11 amino acids derived from the amino-terminus of the spoVG protein, two amino acids derived as a result of DNA manipulations during ligations, followed by the final 45 amino acids from the gp120 envelope protein and the entire gp41 protein sequence. This protein is referred to as recombinant gp41.

f. Transformation:

The plasmid pOM10 was transformed into protoplasts of *B. megaterium* strain PV361 (a prototrophic derivative of strain QMB1551 cured of native plasmids) and viable chloramphenicol resistant cells were allowed to regenerate. Expression of rp41 antigen is under the control of the spoVG promoter and is observed when the cells enter the sporulation growth phase. This plasmid replicates as an independent element, is non-mobilizable, and is maintained at approximately 10 to 30 copies per cell.

ii. Construction of HIV-1 env Vector pTB319 (for Expression of Insoluble HIV-1 gp41) and Introduction into a Host Cell:

The construction of this recombinant *E. coli* clone expressing the HIV-1 CKS-120/41 fusion antigen was carried out in several steps. First, the gene for the rp41 portion of the HIV-1 antigen was synthesized and inserted into a modified pUC18 giving the plasmid pTB315. Next, the DNA sequence coding for the 42 carboxyl amino acids of the gplprotein was synthesized and inserted into pTB315 resulting in plasmid pTB316. Finally, the p120/41 gene was transferred to an expression plasmid (pTB210) which allowed efficient expression of the antigen as a fusion protein. The resulting plasmid, pTB319, was isolated and mapped.

a. Construction of plasmid pTB315:

A gene encoding the amino acids 519–673 and 712–863 of the HIV-1 gp160 envelope protein (Ratner, et al., *Nature*, 313:277–284, 1985) was designed to be constructed from a series of synthetic DNA fragments in a pUC18 plasmid derivative.

Fourteen fragments were chemically synthesized, reproducing a portion of the published gp41 sequence. This sequence consists of amino acids 519–673 and 712–863 with a 38 amino acid transmembrane region from amino acids 674–711 deleted. The 14 synthetic fragments were subcloned into pWM500 (Mandecki and Bolling, *Gene*, 68:101–107, 1988), purified and ligated together to form the rp41 portion of the fusion protein. The rp41 portion of the fusion protein, with terminal BamHI and KpnI restriction sites, was inserted into plasmid pMB10.5 digested with BamI and KpnI. The resulting plasmid was designated pTB315.

b. Construction of plasmid pTB316:

A 129 base pair double stranded DNA fragment representing the carboxy-terminus of gp120 was synthesized (311.3 and 311.4) and inserted into the remaining NarI site of pTB315. This fragment was inserted into plasmid pTB315 which was digested with NarI. A plasmid designated pTB316 was isolated and screened such that the orientation of the inserted fragment was in the same orientation as the gp41 gene.

c. Construction of plasmid pTB210:

This plasmid, derived from plasmid pBR322, contains a modified lac promoter fused to a kdsB gene fragment (encoding the first 239 of the entire 248 amino acids of the *E. coli* CMP-KDO Synthetase of CKS protein) and a synthetic linker fused to the end of the kdsB gene fragment. The synthetic linker includes multiple restriction sites for insertion of genes, translational stop signals and the trpA-Rho independent transcriptional terminator. This plasmid encodes 239 amino acids of CKS and 22 amino acids coded for by the synthetic linker.

d. Construction of plasmid pTB319:

Plasmid pTB316 was digested with BamHI and KpnI, and a 1073 bp fragment was isolated. This fragment consisted of the original synthetic rp41 gene with the 42 carboxyl amino acids of the gp120 gene inserted in the proper location. This fragment was inserted into pTB210 which was previously digested with BglII and KpnI. The resulting plasmid, designated pTB319, was isolated and mapped.

e. Complete DNA sequence of plasmid pTB319:

The promoter region, transcriptional start and ribosomal binding site span bases 45–125. The coding region is comprised of sequences derived from the 239 amino acids of the CKS protein (bases 126–842) and the 11 amino acids from the synthetic polylinker (bases 843–875). This is followed by 42 residues of the HIV-1 gp120 (env) (bases 876–1001) and 185 residues of the HIV-1 rp41 (env) (bases 1002–1556). The 38 amino acid deletion of the transmembrane region is between base pairs 1466 and 1467. Finally, there are an additional 14 amino acids (bases 1557–1598) as the result of a frameshift due to a single A/T deletion and a premature translational termination (bases 1599–1601). The DNA sequence coding of the recombinant protein was confirmed by sequencing of the plasmid isolates from production scale fermentation.

f. Recombinant protein encoded by plasmid pTB319:

The plasmid pTB319 encodes a recombinant protein containing 239 amino acids of the CKS protein and 11 amino acids from the pTB210 multiple restriction site linker. This is followed by 42 amino acids from the carboxyl end of HIV-1 gp120, 185 amino acids from the HIV-1 gp41 protein (a truncated protein with a 38 amino acid deletion of amino acids 674–711 [Ratner, et al., *Nature*, 313:277–284, 1985] spanning the gp41 transmembrane region). Finally, there are 14 amino acids resulting from a frameshift and premature termination due to a single A/T deletion between nucleotides 1556 and 1157. This protein is referred to as recombinant pCKS-41 (rpCKS-41) or insoluble HIV-1 gp41.

g. Transformation:

The plasmid pTB319 was transformed into *E. coli* K-12 strain XL-1 (recA1, endA1, gyrA96, thi-1, hsdR17, supE44, relA1, lac⁻/F', proAB, lacI$^q$ZdeltaM15, TN10 cells made competent by the calcium chloride method. In this construction the expression of the rpCKS-41 protein is under the control of the lac promoter. Recombinant pCKS-41 expression is induced by the addition of IPTG to 100 μg/ml. This plasmid replicates an independent element, is non-mobilizable and is maintained at approximately 10 to 30 copies per cell.

iii. Construction of Vector pKRR955 (for Expression of HIV-1 p24) and Introduction into a Host Cell:

The construction of the rp24 gag expression vector was a multi-step process. The first step involved the construction of an *E. coli* plasmid, pB1, with a smaller gag containing DNA fragment. The second step involved the construction of an expression vector, designated pKRR951, with the proper molecular signals to allow efficient expression. Finally, molecular information was added to the plasmid to allow regulation of gene expression resulting in the final plasmid pKRR955.

a. Construction of plasmid pB1:

A 949 bp BglII/PvuII DNA fragment obtained from plasmid pcR23 was ligated into the plasmid pUC9 (Pharmacia) previously digested with HincII and BamHI. A clone containing a part of the gag gene (including the rp24 coding region) in the same orientation as the lacZ gene was identified, mapped and designated pB1.

b. Construction of plasmid pKRR951:

The gag gene DNA fragment was then introduced into an expression vector pKRR810 which placed the gag gene expression under the control of the *E. coli* lambda phage $P_L$ promoter while allowing efficient termination of protein synthesis. A 963 bp DNA fragment containing most of the gag gene was obtained by an EcoRI (complete)/PstI (partial) digestion of plasmid pB1. The synthetic oligonucleotide DNA fragment of 36 bp was added to the gag gene fragment to reconstruct the amino-terminus of the encoded protein and to place an EcoRI site immediately upstream of the initiation codon. This modified fragment was inserted into the EcoRI site of the expression vector pKRR810. A clone (pKRR950) with the gag gene in the same orientation as the phage $P_L$ promoter was identified, isolated and mapped. The size of this clone was reduced by 106 bp by ApaI digestion and re-ligation of the pKRR950 plasmid resulting in a plasmid designated pKRR951.

c. Construction of plasmid pKRR955:

To complete the construction of the expression vector, the lambda cI$_{ts}$ regulatory gene and the *E. coli* lambda phage $P_R$ promoter were included within the construct. The addition of this temperature sensitive gene allows control of the lambda promoters and subsequently of the gag gene expression. A 2392 bp DNA fragment containing the lambda cI$_{ts}$ regulatory gene and the *E. coli* lambda phage PR promoter was obtained via BglII digestion of a plasmid called pRK248. cI$_{ts}$. This fragment was inserted into the BglII site of plasmid pKRR951 resulting in plasmid pKRR955.

d. Complete DNA sequence of plasmid pKRR955:

The promoter region, transcriptional start and ribosomal binding site span bases 7757–271. This region is derived from two different lambda phage mutants and a synthetic region. The coding region is comprised of a synthetic sequence which duplicates the NH2 end of the lacZ gene from pUC9 (bases 272–307), sequences coding for a portion of the HIV-1 gag gene (bases 308–1183) including the entire rp24 sequence (bases 344–1036), followed by a short sequence from the synthetic three frame translation terminator of the vector pKRR810 (bases 1169–1180). Translation is terminated at the third termination codon in this segment (bases 1181–1183). The sequence shows the rrnBt, transcription terminator (bases 1184–1241).

e. Recombinant protein encoded by plasmid pKRR955:

The plasmid pKRR955 produces a fusion protein comprised of 12 amino acids derived from the lacZ protein and the pUC9 polylinker region, followed by a portion of the gag protein (including the final 12 amino acids of the p17 protein, the entire 231 amino acids of the rp24 protein and the first 44 amino acids of the p15 protein), followed by 4 amino acids derived from the terminator portion of the pKRR810 vector. This protein is referred to as recombinant p24 (re24).

f. Transformation:

The plasmid PKRR955 was transformed into *E. coli* K-12 strain KRR136 (Dlac-pro, supE, thi-1, rpsL, sbcB15, endA, hsdR4, lon-9, tsx:-462:Tn10/F', traD36, ProAB⁺ lacI$^q$zdeltaM15) cells made compete by the calcium chloride method. In this construction the expression or rp24 protein is under the control of both the lambdaP$_L$ and lambda $P_R$ promoters and the cI$_{ts}$ repressor expressed from the cI$_{ts}$ gene present on the plasmid. Recombinant p24 expression is induced by temperature shift from 30 C. to 42 C. This plasmid replicates as an independent element, is non-mobilizable and is maintained at approximately to 30 copies per cell.

iv. Construction of Vector pJC104 for Expression of HIV-2 p36 and Introduction into a Host Cell:

The construction of this recombinant *E. coli* clone expressing the rp41 HIV-2 antigen was carried out in two steps. First, a fragment of the HIV-2 env gene was isolated from a HIV-2 prophage and subcloned in an *E. coli* expression vector designated pEHa. Second, a HIV-2 env gene fragment was subcloned from plasmid pEHa into an alternative expression vector, pTB210N, resulting in the plasmid pJC104.

a. Construction of plasmid pEHa:

A DNA fragment containing the env gene from HIV-2 (prophage isolated D194.5) was identified within a lambda genomic library of prophage DNA. This fragment was subcloned into an EcoRI site of an *E. coli* expression vector (lambda $P_L$ vector pKH20). The resulting plasmid was named pEHa. This work was done by Diagen GmbH, Neiderheider Strasse 3, 4000 Dusseldorf (Kuhnel, et al., *Proc. Natl. Acad. Sci. USA*, 86:2383–2387, 1989).

b. Construction of plasmid pTB210N:

The cloning vector pTB210 allows the fusion of recombinant genes to the CKS protein. This plasmid consists of the plasmid pBR322 with a modified lac promoter fused to a kdsB gene fragment (encoding the first 239 of the entire 248 amino acids of the *E. coli* CMP-KDO Synthetase or CKS protein) and a synthetic linker fused to the end of the kdsB gene fragment. The synthetic linker includes: multiple restriction sites for insertion of genes, translational stop signals and the trpA-Rho independent transcriptional terminator. The plasmid pTB210N contains a NcoI site in the synthetic linker and is derived from the plasmid pTB210.

c. Construction of plasmid pJC104:

Plasmid pEHa was digested with NcoI and a 314 base pair fragment encoding the first 104 amino acids of the HIV-2 gp41 protein was isolated and inserted into the NcoI site of plasmid pTB210N. This plasmid, designated PJC104, expresses the HIV-2 env protein as a fusion with the CKS protein.

d. Complete DNA sequence of plasmid pJC104:

The promoter region, transcriptional start and ribosomal binding site span bases 45–125. The coding region is comprised of sequences derived from the 239 amino acids of the CKS protein (bases 126–842) and the 13 amino acids from the synthetic polylinker (bases 843–881). This is followed by 104 residues of the amino end of the HIV-2 env (bases 882–1193) and 15 amino acids of the remainder of the polylinker (bases 1194–1238). The translation is terminated at the termination codon at bases 1239–1241.

e. Recombinant protein encoded by plasmid pJC104:

The plasmid pJC104 encodes a recombinant protein containing the first 239 amino acids of the CKS protein, 13 amino acids from the pTB210N multiple restriction site linker, 104 amino acids from the HIV-2 env protein (amino acids 506–609 of the HIV-2 env protein) and an additional 15 amino acids from the pTB21ON multiple restriction site linker. This protein is referred to as HIV-2 recombinant pCKS-41 (HIV-2 rpCKS-41).

f. Transformation:

The plasmid pJC104 was transformed into $E.$ $coli$ K-12 strain XL-1 (recA1, end A1, gyrA96, thi-1, hsdR17, supE44, relA1, lac $^-$/F', proAB, lacI$^q$ZdeltaM15, TN10) cells made competent by the calcium chloride method. In this construction, the expression of the rp41 HIV-2 fusion protein is under the control of the lac promoter. Recombinant p41 HIV-2 expression is induced by the addition of IPTG to 100 µg/ml. This plasmid replicates as an independent element, is non-mobilized and is maintained at approximately 10 to 30 copies per cell.

B. Coating of Microparticles:

i. Microparticles coated with HIV-1 gp41 antigen were prepared in the following manner:

Briefly, microparticles at 2% weight/volume (0.25–0.3 microns, Seradyne, Indianapolis, Ind.) was mixed with HIV-1 rp41 (pOM10/pV361) antigen at 200 ug/ml in Tris Buffer, pH 7.0, and tumbled for overnight at room temperature. The so-prepared microparticles then cleaned by centrifugation by cleaned by centifugation for several times and finally resuspended in Phosphate Buffer, pH 7.7 containing 0.1% Tween20. The microparticles then were resuspended in Phosphate Buffer containing 8% sucrose and 50 mM EDTA to a final concentration of 1.0% (w/v).

ii. Microparticles coated with HIV-2 gp36 antigen were prepared in the following manner:

Briefly, microparticles at 0.5% weight/volume (0.25–0.3 microns, Seradyne, Indianapolis) were mixed with HIV-1 gp41 at 200 ug/ml in Tris Buffer, pH 7.0, and tumbled overnight at room temperature. The so-prepared microparticles were then cleaned by centrifugation for several cycles and finally resuspended in Phosphate Buffer, pH 7.7, containing 0.1% Tween20. The microparticles were then resuspended in Phosphate Buffer containing 8% sucrose and 50 mM EDTA to a final concentration of 0.25% (w/v).

iii. Microparticles coated with HIV p24 antigen were prepared in the following manner:

Briefly, microparticles at 1% weight/volume (2.5–3.0 microns, Polyscience (Warrington, Pa.) were mixed with HIV-1 rP24 antigen at 6 ug/ml in Carbonate Buffer, pH 9.3, and tumbled for 24 hours at 37 degrees Celsius. The so-prepared microparticles were then cleaned by centrifugation for several cycles and finally resuspended in Phosphate Buffer containing 8% sucrose and 50 mM EDTA to a final concentration of 0.5%.

EXAMPLE VI

PREPARATION OF PRE-COMPLEXED BIOTINYLATED RECOMBINANT HIV ANTIGENS p24, p36 and gp41 AND ACRIDINIUM-LABELED ANTI-BIOTIN CONJUGATE A. Biotinylation of HIV-1 gp41 with NHS-Biotin (Biotin-XX-NHS Ester, Clonetech (Cat. No. 5008-1)):

HIV-1 p41 antigen was biotinylated at a concentration of 0.9 mg/ml in the biotinylation buffer (bicarbonate buffer, pH 8.5). The biotin was added to 0.155 mg per mg of antigen. The reaction was then allowed to proceed for 3 hours at room temperature. The biotinylated antigen was then dialyzed against Borate/SDS buffer.

B. Biotinylation of HIV-2 gp36 with NHS-Biotin (Biotin-XX-NHS Ester, Clonetech (Cat. No. 5008-1)):

HIV-2 gp36 antigen was biotinylated at a concentration of 1.5 mg/ml in biotinylation buffer (bicarbonate buffer, pH 8.5). The biotin was added to 0.1 mg per mg of antigen. The reaction was allowed to proceed for 3 hours at 2 to 8 degrees Celsius. The biotinylated antigen was then dialyzed against Borate buffer.

C. Biotinylation of HIV-1 p24 with NHS-Biotin (Biotin-XX-NHS Ester, Clonetech (Cat. No. 5008-1)):

HIV-1 p24 antigen was biotinylated at a concentration of 0.2 mg/ml in a biotinylation buffer (Bicarbonate buffer, pH 9.0). The biotin was added to 0.735 mg per mg of antigen. The reaction was allowed to proceed for 4 hours at 2 to 8 degrees Celsius. The biotinylated antigen was then dialyzed against Borate buffer.

Methyl acridinium was labeled to anti-biotin as described hereinabove in Example II(a). Biotinylated recombinant HIV antigens, as described above, were biotinylated, as illustrated above. The degree of functional biotin incorporated to this biotinylated probe was determined by fluorescence polarization following the method described in Clinical Chemistry 40(11):2112 (1994) and was found to be 2–4 moles of biotin/mole of HIV-1/HIV-2 recombinant proteins.

Methyl acridinium labeled anti-biotin antibody was allowed to react with biotinylated probes to make a pre-complex by adding 9 µl of anti-biotin methyl acridinium (690 µg/ml) to pre-mixed 833 µl of biotinylated gp41 (24 µg/ml), 833 µl of biotinylated gp36 (24 µg/ml), and 625 µl of biotinylated p24 (1.6 µg/ml). The reaction mixture was diluted with 2.7 ml of conjugate diluent (phosphate buffer saline, with Triton X-100 and protein stabilizers). This mixture was mixed for 30 minutes at room temperature in the dark, and then stored at 2 to 8 degrees C. overnight. Then, 1 ml of the mixture was diluted to 20 ml with HIV Probe diluent (borate buffer with CKS lysate, calf serum and protein stabilizers; preservative: sodium azide). This so-formed pre-complex was filtered through a 0.2 microm Nalgene membrane. The filtered precomplex was stored at 2–8 degrees Celsius in the dark.

EXAMPLE VII

HIV-1/HIV-2 THREE-STEP ASSAY

At station 1, 100 µL of control or sample and 50 µL of p-41/p-24/HIV-2 coated microparticles (blend of three individual particles; approx. concentration p41 (6 µl (1%)), gp36

(20 µl (0.25%)), p24 (3 µl (0.5%))) were dispensed into the incubation well of a reaction tray. At station 4, the reaction mixture was transferred to the glass fiber matrix of the reaction tray after 18 minutes of incubation at 37 degrees C. At station 5, 50 µL of biotinylated p-24/p-41/HIV-2 (blend of three individual probes) were dispensed onto the glass fiber matrix of the reaction well. The tray was further incubated at 37 degrees Celsius for 10 minutes. At station 6, the transferred microparticles and excess probe were washed. At station 7, 50 µL of acridinium labeled anti-biotin conjugate were dispensed onto the glass fiber matrix of the reaction tray. The tray was further incubated at 37 degrees Celsius for 10 minutes. At station 8, the excess conjugate was washed away. At station 9, a chemiluminescence (CL) signal was activated, and the photons were measured by a photomultiplier tube. The results are expressed as Positive to Negative (P/N) as shown in Table II below.

EXAMPLE VIII

HIV-1/HIV-2 TWO-STEP ASSAY

At station 1, 50 µL of sample or control, 50 µL of Specimen Diluent Buffer (SDB) and 50 µL pf p-41/p-24/HIV-2 coated microparticles (blend of three individual particles; approx. concentration p41 (6 µl (1%)), gp36 (20 µl (0.25%)), p24 (3 µl (0.5%))) were dispensed into the incubation well of a reaction tray. At station 4, the reaction mixture was transferred to the glass fiber matrix of the reaction tray after 18 minutes of incubation at 37 degrees Celsius. At station 5, 50 µL of a pre-complex of biotinylated p-24/p-41/HIV-2 (probe, blend of three individual probes; see Example VI for a discussion of the construction of pre-complexes) and acridinium-labeled anti-biotin were dispensed onto the fiber matrix of the reaction tray. The tray was further incubated for 23 minutes at 37 degrees Celsius. At station 8, the excess complex was washed away. At station 9, a chemiluminescence (CL) signal was activated, and the photons were measured by a photomultiplier tube. The results are expressed as Positive to Negative (P/N) in Table II below.

TABLE II

HIV-1/HIV-2 2-Step vs. 3-Step Assay on the PRISM Format

| POSITIVE | | NEGATIVE** | | HIV-1 | | HIV-2 | |
|---|---|---|---|---|---|---|---|
| 2 step P/N | 3 step P/N | 2 step | 3 step | 2 step P/N | 3 step P/N | 2 step P/N | 3 step P/N |
| 17.79 | 11.08 | 1.145 | 4.911 | 15.52 | 19.05 | 3.55 | 4.62 |

*The P/N is the average chemiluminescence count (n = 2) of the test sample divided by the average chemiluminescence count (n = 2) of the negative sample (n = 2).
**Value for negative calibrator is represented in absolute counts.
Positive calibrator: Human plasma negative using FDA licensed kit for syphilis, HbsAg and HCV antibodies, positive to HIV-1.
HIV-1 panel member: HTV-1 is a mouse monoclonal antibody to HIV-1 p41 antigen.
HIV-2 calibrator: Plasma unit negative using an FDA licensed kit for syphilis, HbsAg and HCV antibody and Western blot positive for antibodies to HIV-2.
As evidenced by the above data, the two step assay gave a comparable P/N to the three step assay.

EXAMPLE IX

PREPARATION OF HTLV MICROPARTICLES

Coating of Microparticles:

The procedure for coating HTLV-I and HTLV-II microparticles are identical, the only difference being the lysate antigen. Briefly, 4 mg/ml of EDAC was added to carboxylated microparticles (3% weight/volume (0.19 microns, Seradyne, Indianapolis, Ind.)) in MES buffer. Either HTLV-I or HTLV-II lysate antigen was added to the microparticle/EDAC mixture at 30 mg/L. The microparticles were mixed at room temperature for 16 to 24 hours. The so-prepared microparticles were then cleaned by centrifugation for several cycles and finally resuspended in Phosphate Buffer containing sucrose and EDTA to a final concentration of 1.0% (w/v).

EXAMPLE X

PREPARATION OF PRE-COMPLEXED BIOTINYLATED HTLV-I AND HTLV-II ENVELOPE-ENRICHED VIRAL LYSATE AND ACRIDINIUM-LABELED ANTI-BIOTIN CONJUGATE

HTLV Cell Banks:

1. HUT 102-B2/HTLV-I (Advanced Biotechnology Vendor)
2. WIL-NRA/HTLV-II Working Cell Bank A. Preparation of Viral Lysates:

The viral lysates were prepared as follows:

HLTV-I was isolated from cell line HUT-102 (Advanced Biotechnologies, Inc., Bethesda, Md.). HUT-102:B2 is a clone of HUT-102 (available from the American Type Culture Collection, Manassas, Va.), and produces the same virus as HUT-102. HTLV-II was isolated from NRA infected cell line WIL-NRA (deposited by Abbott Laboratories with the ATCC and having ATCC. No. CRL 11580; see WO 95/01457 which enjoys common ownership with the present invention and is hereby incorporated in its entirety by reference). The WIL-RNA cell line is produced from cocultivation of peripheral blood lymphocytes with EBV-transformed B-cell line, WIL-2. First, the viruses were grown in tissue culture. A serum-containing medium was used, such as PRMI-1640 (Gibco BRL, Gaithersburg, Md.) supplemented with 10% fetal bovine serum. The viruses excreted into the culture medium were then harvested and used to prepare the lysates. The cells in which the viruses were grown were not lysed.

The harvested viruses were purified by continuous flow ultracentrifugation and passed over a 20%–45% sucrose density gradient using a CF32 rotor. Intact virus was selected based on buoyant density of 1.15 for HTLV-I and 1.14 for HTLV-II. Sucrose concentrations from 28.5% to 38.7% were pooled. Next, the pooled viruses were lysed using 0.25% Triton X100 in Tris saline buffer (10 mM Tris, 150 mM NaCl) and sonication, followed by centrifugation. The supernatant obtained after centrifugation contained the viral lysate. (See also insert corresponding to ABBOTT PRISM® HTLV-1 and HTLV-II assay, Abbott Laboratories, Abbott Park, Ill.)

In order to envelope-enrich the HTLV-I lysate, it was poured over a lentil/lectin column. Biotin was then added, and ammonium sulfate was used for recovery.

B. Biotinylation of HTLV-I Antigen with NHS-Biotin:

HTLV-I viral lysate was biotinylated (Biotin-XX-NHS Ester, Clonetech (Cat. No. 5008-1) at a concentration of 0.5 mg/mL in Borate buffer, pH 8.5. The biotin was added at 0.4 mg per mg of antigen. The reaction was allowed to proceed at 2 to 8 degrees Celsius for 16 to 24 hours. The biotinylated antigen was then dialyzed against Tris/NaCl/Triton X-100 Buffer.

C. Biotinylation of HTLV-II Antigen:

HTLV-II viral lysate was biotinylated at a concentration of 0.2 mg/ml in Borate buffer, pH 8.5. The biotin was added at 0.4 mg per mg of antigen. The reaction was allowed to proceed at 2 to 8 degrees Celsius for 16 to 24 hours. The biotinylated antigen was then dialyzed against Tris/NaCl/Triton X-100 Buffer.

D. Biotinylation of HTLV-I Envelope-Enriched Viral Lysate:

HTLV-I envelope-enriched viral lysate was biotinylated at a concentration of 0.2 mg/ml in a Borate/methyl glucopyranoside/Triton buffer. The biotin was added at 0.8 mg per mg of antigen. The reaction was allowed to proceed at 2 to 8 degrees Celsius for 16 to 24 hours. The biotinylated antigen was then dialyzed against Tris/NaCl/Triton X-100 buffer.

Methyl acridinium labelled anti-biotin antibody was allowed to react with biotinylated probes (as described above) to make a pre-complex by adding 9 µl of anti-biotin methylated acridinium (690 µg/ml) to 340 µl of pre-mixed biotinylated HLTV-I lysate (2 µg/ml), 170 µl of biotinylated HLTV-II lysate (4 µg/ml), and 85 µl of HTLV-I envelope-enriched viral lysate (16 µg/ml). The reaction mixture was diluted with 4.396 ml of conjugate diluent (i.e., phosphate buffered saline, with Triton X-100 and protein stabilizers). This mixture was mixed for 30 minutes in the dark and then stored at 2 to 8 degrees C. overnight. One ml of the mixture was then diluted to 20 ml in Tris buffered saline with calf serum and protein stabilizers. The material was then filtered through a 0.2 micron Nalgene membrane. The filtered pre-complex was stored at 2 to 8 degrees C. in the dark.

EXAMPLE XI

HTLV-1/HTLV-2 THREE-STEP ASSAY

At station 1, 100 µL of control or sample and 50 µL of HTLV-1/HTLV-2 coated microparticles (blend of two particles; approx. concentration of 0.1% (w/v); ratio of HTLV-1 to HTLV-2 microparticles=3:2) were dispensed into the incubation well of a reaction tray. At station 4, the reaction mixture was transferred to the glass fiber matrix of a reaction tray after 18 minutes of incubation at 37 degrees Celsius. At station 5, 50 µL of biotinylated HTLV-1/HTLV-2 (probe, blend of HTLVI lysate, HTLVII lysate and HLTVI enriched viral lysate probes) were dispensed onto the glass fiber matrix of a reaction tray. The tray was further incubated at 37 degrees Celsius for 10 minutes. The transferred microparticles and excess complex was washed. At station 7, 50 µl microliters of acridinium-labeled anti-biotin conjugate was dispensed onto the glass fiber matrix of the reaction tray. The tray was further incubated at 37 degrees for 10 minutes. At station 8, the excess conjugate was washed away. At station 9, a chemiluminescence (CL) signal was activated, and the photons were measured by a photomultiplier tube. The results are expressed as Positive to Negative (P/N) in Table III.

EXAMPLE XII

HTLV-1/HTLV-2 TWO-STEP ASSAY

At station 1, 50 µL of sample or control, 50 µL of Specimen Diluent Buffer (SDB) and 50 µL of HTLV-1/HTLV-2 coated microparticles (blend of two particles; approx. concentration of 0.1% (w/v); ratio of HTLV-1 to HTLV-2 microparticles=3:2) were dispensed into the incubation well of the reaction tray. At station 4, the reaction mixture was transferred to the glass fiber matrix of a reaction tray after 18 minutes of incubation at 37 degrees Celsius. At station 5, 50 µL of a pre-complex of biotinylated HTLV-1/HTLV-2 (probe, blend of two probes) and acridinium labeled anti-biotin were dispensed onto the fiber matrix of the reaction tray. The tray is further incubated for 23 minutes at 37 degrees Celsius. At station 8, the excess complex was washed away. At station 9, a chemiluminescence (CL) signal was activated, and the photons were measured by a photomultiplier tube. The results are expressed as Positive to Negative (P/N) in Table III.

TABLE III

HTLV-I/HTLV-II 2-Step vs. 3-Step Assay on the PRISM Format

| POSITIVE | | NEGATIVE** | | HTLV-1 | | HTLV-2 | |
| --- | --- | --- | --- | --- | --- | --- | --- |
| 2 step P/N | 3 step P/N | 2 step | 3 step | 2 step P/N | 3 step P/N | 2 step P/N | 3 step P/N |
| 12.27 | 12.7 | 1.067 | 1.377 | 2.54 | 3.4 | 2.59 | 2.8 |

*The P/N is the average chemiluminescence count (n = 2) of the test sample divided by the average chemiluminescence count (n = 2) of the negative sample (n = 2).
**Value for negative calibrator is represented in absolute counts.

The data in Table III demonstrate that the two step assay gave a comparable P/N to the three step assay.

The two and three step assays are summarized in Tables IV and V below. These tables are presented for illustrative purposes only and do not limit the scope of the invention. Various modifications may be made to the information in these tables. Such modifications are considered to fall within the scope of the invention.

TABLE IV

TWO-STEP ASSAY

| Assay | Sample | Specimen Diluent Buffer | Uparticle | Transfer Wash | Conjugate | Conjugate Wash |
| --- | --- | --- | --- | --- | --- | --- |
| HIV ½ Components | Serum/ Plasma | Borate Buffer pH 8.3 | Polystyrene coated with HIV1, HIV2 antigens in Sucrose buffer, pH 7.0 | LDS/Borate/NaCl buffer, pH 8.5 | Precomplex of (Biotinylated HIV1, HIV2 antigens) : (Anti-Biotin/Acridinium) | Tris/LiCl₂/LDS Buffer, pH 8.0 |
| HIV ½Assay Volumes (uL) | 100 | 50 | 1 × 50 | 2 × 300 | 1 × 50 | 3 × 100 |
| Dispense Station Number | 1 | 1 | 1 | 4 | 5 | 8 |
| HTLVI/II Components | Serum/ Plasma | Tris/NaCl pH 8.3 | Polystyrene coated with HTLV I, HTLV | Phosphate buffered saline, pH 7.2 | Precomplex of (Biotinylated HTLVI1, HTLVII, gb46 | Tris/NaCl /Triton X-100 Buffer, pH |

TABLE IV-continued

TWO-STEP ASSAY

| Assay | Sample | Specimen Diluent Buffer | Uparticle | Transfer Wash | Conjugate | Conjugate Wash |
|---|---|---|---|---|---|---|
| | | | II Antigens in Sucrose buffer pH 7.5 | | antigens) : (Anti-Biotin/Acridinium) | 8.0 |
| HTLVI/II Assay Volumes (uL) | 100 | 50 | 1 × 50 | 2 × 300 | 1 × 50 | 3 × 100 |
| Dispense Station Number | 1 | 1 | 1 | 4 | 5 | 8 |
| Chagas Assay Components | Serum/Plasma | SOD/E-Coli Lysate/Octoxynol/Borate/Tween-20/Celquat/Albumin buffer, pH 7.5 | Polystyrene coated with Chagas antigens, pH 7.0 | Borate/Polysorbate/Glycerol/NaCl Buffer, pH 7.0 | Precomplex of (Biotinylated Anti-Human antibody) : (Anti-Biotin/Acridimium) | MES/NaCl/Proclin Buffer pH 5.7 or Borate/LDS Azide pH 8.5 |
| Chagas Assay Volumes (uL) | 50 | 1 × 50 | 1 × 50 | 2 × 300 | 1 × 50 | 5 × 100 |
| Chagas Dispense Station Number | 1 | 1 | 1 | 4 | 5 | 8 |

LDS = Lithium Dodecyl Sulfate
SOD = Superoxide Dismutase

TABLE V

THREE-STEP ASSAY

| Assay | Sample | Specimen Diluent Buffer | Uparticle | Transfer Wash | Probe | Probe Wash | Conjugate | Conjugate Wash |
|---|---|---|---|---|---|---|---|---|
| HIV ½ Components | Serum/Plasma | None | Polystyrene coated with HIV1, HIV2 antigens in Sucrose buffer pH 7.0 | LDS/Borate/NaCl buffer pH 8.5 | Biotinylated HIV 1, HIV 2 antigens | Tris/LiCl₂/LDS Buffer pH 8.0 | Anti-Biotin/Acridinium | MES/NaCl Buffer pH 5.7 |
| HIV ½Assay Volumes (uL) | 100 | n/a | 1 × 50 | 2 × 300 | 1 × 50 | 4 × 100 | 1 × 50 | 5 × 100 |
| HIV Dispense Station Number | 1 | 1 | 1 | 4 | 5 | 6 | 7 | 8 |
| HTLVI/II Components | Serum/Plasma | None | Polystyrene coated with HTLV I, HTLV II Antigens in Sucrose buffer pH 7.5 | Phosphate buffered saline pH 7.2 | Biotinylated HTLVI, HTLVII, gp46 antigens pH 8.0 | Tris/NaCl/Triton X-100 buffer | Anti-Biotin/Acridinium | MES/NaCl Buffer pH 5.7 |
| HTLVI/II Assay Volumes (uL) | 100 | n/a | 1 × 50 | 2 × 300 | 1 × 50 | 3 × 100 | 1 × 50 | 3 × 100 |
| HTLV Dispense Station Number | 1 | 1 | 1 | 4 | 5 | 6 | 7 | 8 |
| Chagas Assay Components | Serum/Plasma | SOD/E-coli Lysate/Octoxynol/Borate/Tween-20/Celquat/Albumin buffer pH 7.5 | Polystyrene coated with Chagas antigens pH 7.0 | Borate/Polysorbate/Glycerol/NaCl Buffer pH 7.0 | Biotinylated Anti-Human antibody | Tris/LiCl₂/LDS Buffer pH 8.0 | Anti-Biotin/Acridinium | MES/MaCl Buffer pH 5.7 |
| Chagas Assay Volumes (uL) | 50 | 1 × 50 | 1 × 50 | 2 × 300 | 1 × 50 | 4 × 100 | 1 × 50 | 5 × 100 |
| Chagas Dispense Station Number | 1 | 1 | 1 | 4 | 5 | 6 | 7 | 8 |

LDS: Lithium Dodecyl Sulfate

What is claimed is:

1. A method for determining the presence of a Chagas Disease analyte in a test sample by specific amplification of a chemiluminescent signal generated from a heterogeneous immunoasssay comprising the steps of:
    a. incubating a test sample containing a Chagas Disease analyte with an analyte-specific binding pair member for a time and under conditions sufficient to form analyte/analyte specific-binding member pair complexes;
    b. contacting the analyte/analyte-specific binding member pair complexes with a precomplex wherein said precomplex comprises 1) a probe comprising an enhancer compound attached to an analyte-specific binding member different from said analyte-specific binding member of step (a) and 2) a conjugate comprising a chemiluminescent signal generating compound attached to an enhancer-specific binding member, and incubating said resulting mixture for a time and conditions sufficient to form analyte/analyte-specific binding member pair/precomplex complexes wherein said chemiluminescent signal generating compound is an acridinium compound or a derivative thereof;

c. separating said resulting analyte/analyte-specific binding member pair/precomplex complexes of step b from free, unbound precomplexes; and d. determining the presence of said Chagas Disease analyte in said test sample by measuring the detectable signal.

2. The method of claim 1 wherein said analyte is an antibody or an antigen.

3. The method of claim 1 wherein said enhancer compound is selected from the group consisting of a hapten, a fluorescent compound and di-nitrophenol.

4. The method of claim 1 wherein said enhancer compound is biotin.

5. The method of claim 1 wherein said acridinium compound is selected from the group consisting of an acridinium ester and an acridinium sulfonamide.

6. The method of claim 1 wherein said analyte-specific binding member is attached to a solid phase prior to step (a).

7. A kit for detecting a Chagas Disease analyte, comprising a Chagas disease analyte-specific binding pair member; and a single container containing a precomplex reagent wherein said precomplex reagent comprises 1) a probe which comprises an enhancer compound and 2) a conjugate which comprises a chemiluminescent signal-generating compound, wherein said chemiluminescent signal-generating compound is an acridinium compound.

8. The kit of claim 7 wherein said enhancer compound is selected from the group consisting of a hapten, a fluorescent compound and di-nitrophenol.

9. The kit of claim 7 wherein said enhancer compound is biotin.

10. The kit of claim 7 wherein said acridinium compound is selected from the group consisting of an acridinium ester and an acridinium sulfonamide.

11. A method for determining the presence of an HTLV analyte in a test sample by specific amplification of a chemiluminescent signal generated from a heterogeneous immunoasssay comprising the steps of:

a. incubating a test sample containing an HTLV analyte with a biotinylated lysate comprising an analyte-specific binding pair member for a time and under conditions sufficient to form analyte/analyte specific-binding member pair complexes;

b. contacting the analyte/analyte-specific binding member pair complexes with a precomplex wherein said precomplex comprises 1) a probe comprising an enhancer compound attached to an analyte-specific binding member which may be either the same or different from said analyte-specific binding member of step (a) and 2) a conjugate comprising a chemiluminescent signal generating compound attached to an enhancer-specific binding member, and incubating said resulting mixture for a time and conditions sufficient to form analyte/analyte-specific binding member pair/precomplex complexes wherein said chemiluminescent signal generating compound is an acridinium compound or a derivative thereof;

c. separating said resulting analyte/analyte-specific binding member pair/precomplex complexes of step b from free, unbound precomplexes; and d. determining the presence of said HTLV analyte in said test sample by measuring the detectable signal.

12. The method of claim 11 wherein said analyte is an antibody or an antigen.

13. The method of claim 11 wherein said enhancer compound is selected from the group consisting of a hapten, a fluorescent compound and di-nitrophenol.

14. The method of claim 11 wherein said enhancer compound is biotin.

15. The method of claim 11 wherein said acridinium compound is selected from the group consisting of an acridinium ester and an acridinium sulfonamide.

16. The method of claim 11 wherein said analyte-specific binding member is attached to a solid phase prior to step (a).

17. A kit for detecting a HTLV analyte, comprising a HTLV analyte-specific binding pair member; and a single container containing a precomplex reagent wherein said precomplex reagent comprises 1) a probe which comprises an enhancer compound and 2) a conjugate which comprises a chemiluminescent signal-generating compound, wherein said chemiluminescent signal-generating compound is an acridinium compound.

18. The kit of claim 17 wherein said enhancer compound is selected from the group consisting of a hapten, a fluorescent compound and di-nitrophenol.

19. The kit of claim 17 wherein said enhancer compound is biotin.

20. The kit of claim 17 wherein said acridinium compound is selected from the group consisting of an acridinium ester and an acridinium sulfonamide.

21. A method for determining the presence of an HIV analyte in a test sample by specific amplification of a chemiluminescent signal generated from a heterogeneous immunoasssay comprising the steps of:

a. incubating a test sample containing an HIV analyte with a biotinylated analyte-specific binding pair member for a time and under conditions sufficient to form analyte/analyte specific-binding member pair complexes;

b. contacting the analyte/analyte-specific binding member pair complexes with a precomplex wherein said precomplex comprises 1) a probe comprising an enhancer compound attached to an analyte-specific binding member which may be either the same or different from said analyte-specific binding member of step (a) and 2) a conjugate comprising a chemiluminescent signal generating compound attached to an enhancer-specific binding member, and incubating said resulting mixture for a time and conditions sufficient to form analyte/analyte-specific binding member pair/precomplex complexes wherein said chemiluminescent signal generating compound is an acridinium compound or a derivative thereof;

c. separating said resulting analyte/analyte-specific binding member pair/precomplex complexes of step b from free, unbound precomplexes; and d. determining the presence of said HIV analyte in said test sample by measuring the detectable signal.

22. The method of claim 21 wherein said analyte is an antibody or an antigen.

23. The method of claim 21 wherein said enhancer compound is selected from the group consisting of a hapten, a fluorescent compound and di-nitrophenol.

24. The method of claim 21 wherein said enhancer compound is biotin.

25. The method of claim 21 wherein said acridinium compound is selected from the group consisting of an acridinium ester and an acridinium sulfonamide.

26. The method of claim 21 wherein said analyte-specific binding member is attached to a solid phase prior to step (a).

27. A kit for detecting a HIV analyte, comprising a HIV analyte-specific binding pair member; and a single container containing a precomplex reagent wherein said precomplex reagent comprises 1) a probe which comprises an enhancer compound and 2) a conjugate which comprises a chemiluminescent signal-generating compound, wherein said chemiluminescent signal-generating compound is an acridinium compound.

28. The kit of claim 27 wherein said enhancer compound is selected from the group consisting of a hapten, a fluorescent compound and di-nitrophenol.

29. The kit of claim 27 wherein said enhancer compound is biotin.

30. The kit of claim 27 wherein said acridinium compound is selected from the group consisting of an acridinium ester and an acridinium sulfonamide.

* * * * *